: (12) United States Patent
Lenor

(10) Patent No.: US 9,536,173 B2
(45) Date of Patent: Jan. 3, 2017

(54) METHOD AND DEVICE FOR IMAGE-BASED VISIBILITY RANGE ESTIMATION

(71) Applicant: Robert Bosch GmbH, Stuttgart (DE)

(72) Inventor: Stephen Lenor, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/701,393

(22) Filed: Apr. 30, 2015

(65) Prior Publication Data

US 2015/0317535 A1 Nov. 5, 2015

(30) Foreign Application Priority Data

May 2, 2014 (DE) ........................ 10 2014 208 271

(51) Int. Cl.
| | | |
|---|---|---|
| G06K 9/00 | (2006.01) | |
| G06K 9/46 | (2006.01) | |
| G06T 7/00 | (2006.01) | |
| B60W 40/02 | (2006.01) | |
| G08G 1/16 | (2006.01) | |
| G01N 21/53 | (2006.01) | |

(52) U.S. Cl.
CPC ............ *G06K 9/4661* (2013.01); *B60W 40/02* (2013.01); *G01N 21/538* (2013.01); *G06K 9/00791* (2013.01); *G06T 7/00* (2013.01); *G06T 7/0051* (2013.01); *G06T 7/0079* (2013.01); *G06T 7/0081* (2013.01); *G08G 1/16* (2013.01); *G06T 2207/10016* (2013.01); *G06T 2207/10021* (2013.01); *G06T 2207/10028* (2013.01); *G06T 2207/30252* (2013.01); *G06T 2207/30256* (2013.01)

(58) Field of Classification Search
None
See application file for complete search history.

(56) References Cited

U.S. PATENT DOCUMENTS

| | | | | |
|---|---|---|---|---|
| 2004/0046866 A1* | 3/2004 | Pochmuller | ......... | B60R 16/0237 348/135 |
| 2013/0342692 A1* | 12/2013 | Li | ........................ | G01N 21/538 348/143 |

FOREIGN PATENT DOCUMENTS

| | | |
|---|---|---|
| EP | 1 474 652 | 11/2004 |
| FR | WO2003069275 A1 * | 8/2003 |

OTHER PUBLICATIONS

Bobel, Volker "Function Minimization" University of Hamburg, Mar. 2003, Deutsches Elektronen—Synchrotron (DESY.*
WO 03/069375 PCT Dated Aug. 21, 2003 Lavenant Jean et al.*

* cited by examiner

*Primary Examiner* — Nancy Bitar
(74) *Attorney, Agent, or Firm* — Norton Rose Fulbright US LLP; Gerard Messina

(57) ABSTRACT

A method for image-based visibility range estimation for a vehicle includes: ascertaining a depiction of an object of the surroundings in an image of an image detection device of the vehicle, the object having an extension in the direction of travel of the vehicle, the image showing a depiction of surroundings ahead of the vehicle; segmenting the depiction of the object in order to obtain first and second object ranges of the object having respective first and second distances to the image detection device within respective tolerance ranges; determining a first object luminance of the first object range and a second object luminance of the second object range; and determining an atmospheric extinction coefficient correlated to the visibility range, using the first and second object luminances, and the first and second distances.

8 Claims, 6 Drawing Sheets

METHOD AND DEVICE FOR IMAGE-BASED VISIBILITY RANGE ESTIMATION

CROSS-REFERENCE TO RELATED APPLICATION

This application claims foreign priority benefits under 35 U.S.C. §119 to German Application No. 10 2014 208 271.4, filed on May 2, 2014.

BACKGROUND OF THE INVENTION

1. Field of the Invention

The present invention relates to a method for an image-based visibility range estimation, to a corresponding device for the image-based visibility range estimation, as well as to a corresponding computer program product.

2. Description of the Related Art

With a rapid further development of sensors and systems, an increasingly accurate detection of the vehicle surroundings is made possible. Different driver assistance systems may thus support the human driver in his or her driving task and/or assume parts of the tasks completely. Various active and passive sensors work with the aid of different electromagnetic spectral ranges. Depending on the spectral range, more or less strong dampening and scattering effects may occur due to atmospheric phenomena, for example, rain or fog. For cameras having a spectral range approximately in the area of the visible light, mainly fog may in this way result in visibility limitations.

Published European patent application document EP 1 474 652 A1 describes a method for determining the visibility range, in particular from a vehicle in an environment, and a method for determining the presence of fog.

BRIEF SUMMARY OF THE INVENTION

Against this background, using the approach presented here, a method for the image-based visibility range estimation for a vehicle is presented, furthermore a device for the image-based visibility range estimation for a vehicle which uses this method, and finally a corresponding computer program.

A knowledge of the instantaneous visibility range is advantageous for several systems in a vehicle. From an object luminance of an object in a plurality of different distances, a characteristic may be ascertained which shows a correlation with the visibility range. The object luminance may here be obtained from an image of an image detection system or from an image detection device. In variants of the introduced method, the number of the examined objects, the number of the analyzed images or underlying mathematic models may be varied or combined in order to design the method in a more robust way.

A method is introduced for the image-based visibility range estimation, the method including the following steps: ascertaining a depiction of an object in an image, the image showing a depiction of surroundings of an image detection device;
segmenting the depiction of the object in order to obtain one first object range of the object having an equal first distance within a tolerance range to the image detection device, and a second object range of the object having an equal second distance within a tolerance range to the image detection device, as well as determining a first object luminance for the first object range and an object luminance for the second object range; and
determining an atmospheric extinction coefficient K using the first object luminance, the second object luminance, the first distance and the second distance, atmospheric extinction coefficient K being directly correlated to the visibility range.

The visibility range may be a visibility range prevailing in the surroundings. An image may be understood to mean a depiction of surroundings, for example, of a vehicle, obtained using an image detection device. An object may characterize an area in the image in which an object from the surroundings is depicted. The object may have an extension in a viewing direction of the image detection device. The object may have a depth whereby different object ranges may have different distances to the image detection device. The image may have different intensity data. The object luminance may be understood to mean intensity data of the object. The object luminance may depend on an object light and on an ambient light scattered in. In the step of segmenting, the image may be segmented, in particular, in an area of a center of the image. The object ranges found in the step of segmenting may be characterized by an object luminance remaining constant within a tolerance range and additionally or alternatively by a distance to the image detection device remaining constant within the tolerance range. For each object range, a value pair of object luminance and distance may be provided. A distance may be understood to mean a space. The distance may be a space of the image detection device to the object or item. The object may have a direction independence of the luminance and may be referred to as a diffuse radiator or Lambertian radiator. The object may radiate the same luminance in all direction. The object may have a property of a Lambertian surface element.

The method for the image-based visibility range estimation may be used for or in a vehicle. The method for the image-based visibility range estimation may be used independently of a vehicle in a mobile camera, which, for example, moves in the surroundings. The method may thus be used by a pedestrian, for example, using a smart phone. The method may also be used with a plurality of cameras or image detection devices which are designed to capture an object from different distances. The object may in particular be detected at points in time which are preferably close together. Alternatively, the method for the image-based visibility range estimation may be used using a stationary image detection device.

In the step of ascertaining, a depiction of an object of the surroundings may be ascertained in an image of the image detection device, it being possible for the object to have an extension in the direction of travel of the vehicle and for the image to show a depiction of surroundings ahead of the vehicle.

To describe the fog density, the extinction coefficient $K = K_a + K_s$ [1/m] may be used, which is made up of the scattering coefficient $K_s$ [1/m] and the absorption coefficient $K_a$ [1/m]. The extinction coefficient K may be, for example, directly connected to the human perception using the definition of meteorological visibility range $d_{met}$ [m]:

$$d_{met} = \frac{\log(0.05)}{K} \quad (1)$$

The meteorological visibility range results as the distance at which an object is still perceivable with 5% of its original contrast.

For different reasons it may be interesting to be able to estimate extinction coefficient K. For example, drivers may be warned when they are traveling at a velocity unsuited to the visibility range. The velocity may even be automatically adapted corresponding to the visibility range. Furthermore, the fog density is an interesting variable for sensors and systems which work in the spectral range which is strongly attenuated by fog, for example, camera or LIDAR. These sensors, like humans, may no longer make reliable statements above their meteorological range. For example, when no object is detected 75 m ahead in the case of a visibility range of 50 m, this does not mean that there is no object situated there. Different algorithmic parameters may be adapted to the visibility conditions. Another use may be the control of fog lights, which may be turned on during fog for higher comfort, or the control of the rear fog lights, which must or should be turned on at a visibility range of below 50 m due to regulatory requirements such as the StVo (German highway code, Straβenverkehrsordnung) or to increase safety.

A method and a device are presented which may estimate extinction coefficient K, in particular during daylight, particularly rapidly or real-time-capably from a partially segmented surface and distance data of a camera.

In the step of determining, extinction coefficient K may be determined using a one-dimensional equation. Extinction coefficient K may be determined using a model for light transmission by atmospheric aerosols. Advantageously, a one-dimensional equation and additionally or alternatively a model of horizontal view may enable a more rapid determination of extinction coefficient K. The model of horizontal view may be formulated as a one-dimensional equation.

In the step of determining, extinction coefficient K may be determined using an estimation method from the one-dimensional equation. This makes it possible to approximately and very rapidly determine extinction coefficient K. The estimation method may be carried out iteratively and approach determined extinction coefficient K to critical extinction coefficient K of an objective functional with each iteration.

Advantageously, at least three iterations may be carried out. Advantageously, less than five iterations are sufficient in order to approach determined extinction coefficient K in a favorable tolerance range to critical extinction coefficient K of the objective functional. Critical extinction coefficient K may be different from a "true" extinction coefficient K of the surroundings, it being possible, however, for critical extinction coefficient K to represent a best possible estimation as a minimum of the objective functional.

Extinction coefficient K may be determined in the step of determining using an iterative Newton's method. Advantageously, a trivial method is used for the determination of extinction coefficient K. A real-time-capable determination of extinction coefficient K may thus take place.

In the step of segmenting, the depiction of the object may be segmented in order to obtain at least one third object range having an equal third distance within a tolerance range to the image detection device, and a third object luminance for the third object range may be determined. In the step of segmenting, atmospheric extinction coefficient K may be determined using the third object luminance and the third distance.

In one specific embodiment, the method includes a step of detecting the image using an image detection device, in particular an image detection device of a vehicle. The image represents a depiction of an object of the surroundings in the image. The object may have an extension in a distance and additionally or alternatively in a depth to the image detection device. The object may have an extension in the direction of travel of the vehicle. Advantageously, the image used for the visibility range estimation may thus be detected directly.

The steps of ascertaining and segmenting may be carried out for an additional image. For the additional image, at least one additional object luminance and one additional distance assigned to the depiction of the additional object luminance may be determined. In the step of determining, atmospheric extinction coefficient K may be determined using at least the one additional object luminance and the additional distance assigned to the additional object luminance. The image may be detected at a first point in time. The additional image may be detected at an additional point in time. Atmospheric extinction coefficient K may thus be determined using the first point in time of the detection of the image and of the second point in time of the detection of the additional image.

The approach presented here also provides a device which is designed for carrying out, controlling, or implementing the steps of one variant of a method provided here in appropriate devices. The object on which the present invention is based may also be achieved rapidly and efficiently by this embodiment variant of the present invention in the form of a device.

In the present case, a device may be understood to mean an electrical device which processes sensor signals and outputs control and/or data signals as a function thereof. The device may include an interface which may be designed as hardware and/or software. In a hardware design, the interfaces may, for example, be part of a so-called system ASIC, which includes various functions of the device. However, it is also possible that the interfaces are dedicated integrated circuits or are made, at least in part, of discrete components. In a software design, the interfaces may be software modules, which, for example, are present on a microcontroller together with other software modules.

Also advantageous is a computer program product or computer program including program code which may be stored on a machine-readable carrier or storage medium such as a semiconductor memory, a hard disk memory, or an optical memory, and used for carrying out, implementing, and/or controlling the steps of the method according to one of the above-described specific embodiments, in particular when the program product or program is executed on a computer or a device.

The approach described herein is explained by way of example in greater detail below with reference to the attached drawings.

DETAILED DESCRIPTION OF THE INVENTION

Figure 1:
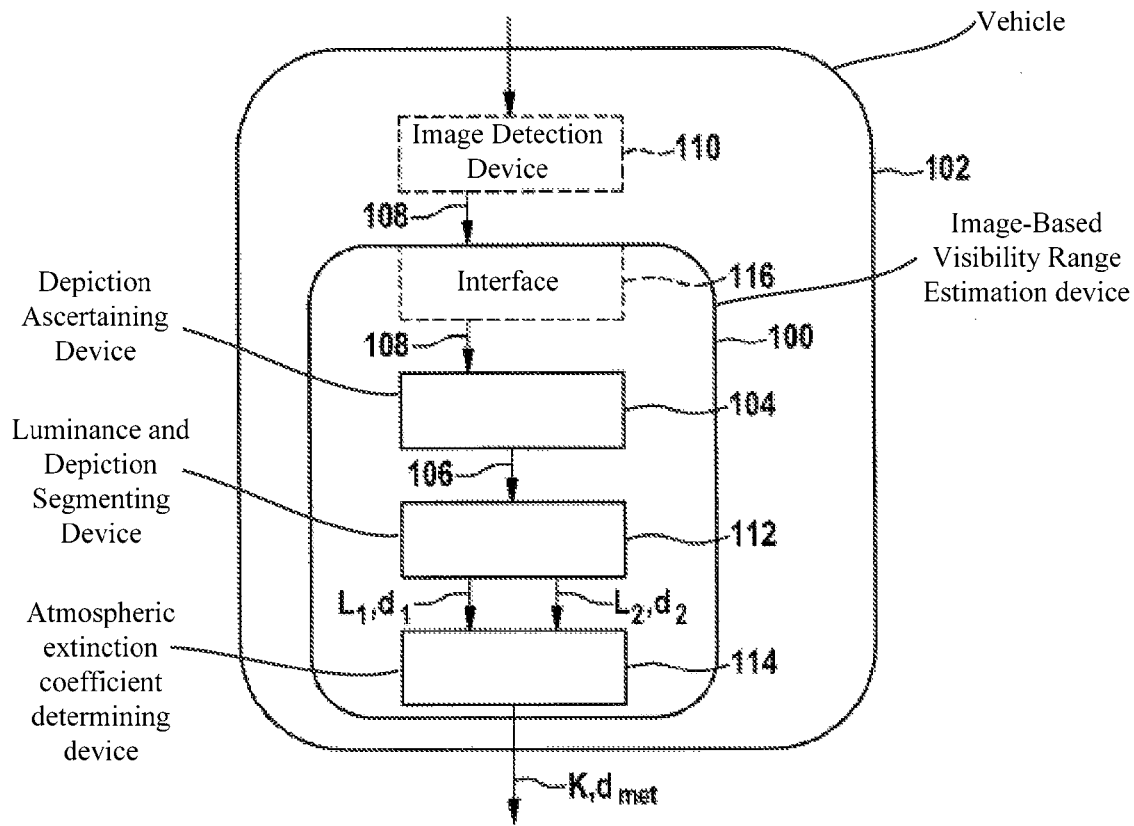
FIG. 1 shows a block diagram of a device for the image-based visibility range estimation for a vehicle according to an exemplary embodiment of the present invention.

In the following description of advantageous exemplary embodiments of the present invention, identical or similar reference numerals are used for elements which are similar operating elements and represented in the various figures, a repeated description of these elements being omitted.

FIG. 1 shows a block diagram of a device 100 for the image-based visibility range estimation for a vehicle 102 according to one exemplary embodiment of the present invention. Device 100 includes a device 104 for ascertaining a depiction 106 of an object of the surroundings in an image 108 of an image detection device 110 of vehicle 102, and a device 112 for segmenting a first object range of the object having an equal first distance $d_1$ within a tolerance range to image detection device 110 and a second object range of the object having an equal second distance $d_2$ within a tolerance range to image detection device 110. Device 112 is furthermore designed to determine a first object luminance $L_1$ for the first object range and a second object luminance $L_2$ for the second object range. Furthermore, device 100 includes a determination device 114 for determining an atmospheric extinction coefficient K using first object luminance $L_1$, second object luminance $L_2$, first distance $d_1$ and second distance $d_2$, atmospheric extinction coefficient K being directly correlated to visibility range $d_{met}$. The correlation between atmospheric extinction coefficient K and visibility range $d_{met}$ is shown in equation (1).

In an alternative exemplary embodiment, image detection device 110 and device 100 for the image-based visibility range estimation is used independently of a vehicle.

Image 108 represents a depiction 106 of surroundings ahead of vehicle 102 according to this exemplary embodiment. The object which is segmented in device 112 for segmenting has an extension in the direction of travel of vehicle 102.

In an alternative exemplary embodiment, the object has an extension in distance or depth to the vehicle. In an alternative exemplary embodiment, the object has an extension in one viewing direction of the image detection device. For example, the road detected by the image detection device describes a curve, or the image detection device has a detection direction which is different from the direction of travel of the vehicle, and the object extending in the depth is, for example, a parking lot or a runway situated next to the vehicle.

Furthermore, in the exemplary embodiment shown in FIG. 1, device 100 includes an interface 116 for reading in image 108. Image 108 is detected using image detection device 110. Image 108 shows an item from the surroundings of image detection device 110 as an object, the distance $d_1$, $d_2$ each representing a distance between image detection device 110 and a segmented object range.

Figure 2:
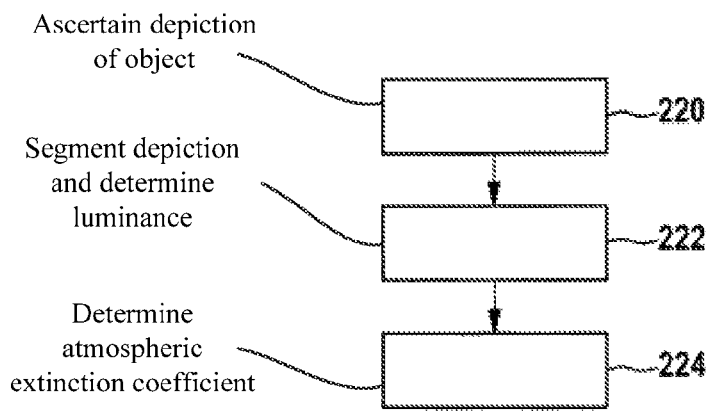
FIG. 2 shows a flow chart of a method for the image-based visibility range estimation according to an exemplary embodiment of the present invention.

FIG. 2 shows a flow chart of a method for the image-based visibility range estimation according to one exemplary embodiment of the present invention. The method may be carried out on the device shown and described with reference to FIG. 1. The method for the image-based visibility range estimation includes a step 220 of ascertaining a depiction of an object in an image of an image detection device, the object having an extension in a viewing direction of the image detection device, a step 222 in which, on the one hand, the depiction is segmented in order to obtain one first object range of the object having an equal first distance $d_1$ within a tolerance range to the image detection device, and a second object range of the object having an equal second distance $d_2$ within a tolerance range to the image detection device, and, on the other hand, a first object luminance $L_1$ is determined for the first object range and a second object luminance $L_2$ is determined for the second object range. The method furthermore includes a step 224 for determining an atmospheric extinction coefficient K using first object luminance $L_1$, second object luminance $L_2$, first distance $d_1$, and second distance $d_2$, atmospheric extinction coefficient K being in direct correlation to visibility range $d_{met}$. The correlation between atmospheric extinction coefficient K and visibility range $d_{met}$ is shown in equation (1).

In one exemplary embodiment, in step 224 of determining, extinction coefficient K is determined using a one-dimensional equation and additionally or alternatively a model of horizontal view.

In one exemplary embodiment, extinction coefficient K is determined in step 224 of determining using an estimation method from the one-dimensional equation.

Optionally, extinction coefficient K is determined in step 224 of determining using an iterative Newton's method.

In step 222 of segmenting, at least one third object range having an equal third distance within a tolerance range to the image detection device is optionally segmented and a third object luminance for the third object range is determined. In the step of determining, atmospheric extinction coefficient K is determined using the third object luminance and the third distance.

The method optionally includes a step of detecting the image using an image detection device of the vehicle, the image showing a depiction of an object of the surroundings in the image, the object having an extension in the direction of travel of the vehicle.

In one exemplary embodiment, the steps of ascertaining 220 and segmenting 222 are carried out for an additional image, atmospheric extinction coefficient K being determined in step 224 of determining using at least third object luminance $L_3$ and a third distance $d_3$ assigned to third object luminance $L_3$. During the process, at least one third object luminance $L_3$ and assigned third distance $d_3$ are ascertained during the execution of the steps of ascertaining 220 and segmenting 222 for the additional image.

As one aspect, this method segments the road area in the middle of the camera image if possible (or other surfaces with a z-extension/depth extension.) In the segmented area, distances to the road are determined (for example, via stereo (stereo camera), via "Structure from Motion" (mainly for mono camera), via knowledge about the road surface (flat earth assumption also possible) and orientation of the camera to the road (mainly for mono camera), via other sensors such as radar and LIDAR (requires good extrinsic calibration of the entire system, however), . . . . ) Road areas of approximately the same distance are combined (for example, line by line for a camera which is hardly rotated) and a luminance for the combined areas is estimated (for example as an average or median luminance.) $N \in \mathbb{N}$ luminance-distance value pairs $(L_1; d_1), \ldots, (L_N; d_N)$ thus result. If an approximately constant reflection of the road is presumed and it is assumed to be a Lambertian surface (realistic assumptions), extinction coefficient K may be determined from the measurements by adapting a fog model (at least in parameters L, d and K) to the measured values. It is advantageous that this method is not dependent on the possibility of segmenting the road completely to the horizon. This is particularly useful in the case of preceding vehicles or otherwise geometrically blocked sight on the course of the road.

One exemplary embodiment of the method described here uses only one single image, not an image sequence including a trackable object. Tracking an object over a long time is replaced here or supplemented by the partial segmentation of the (road) surface.

In one exemplary embodiment, additional surroundings information (e.g., surroundings lightness, object information, . . . ) are taken into account in step 224 of determining. These may be obtained from the image and/or from additional sensors and/or from the context, among others.

Figure 3:
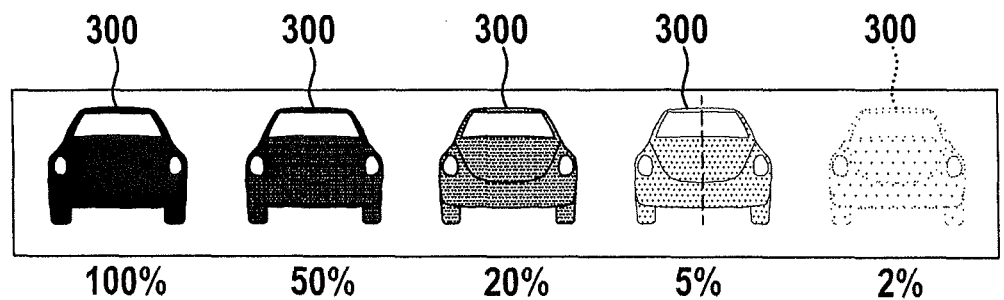
FIG. 3 shows a schematic representation of a meteorological visibility range according to an exemplary embodiment of the present invention.

FIG. 3 shows a schematic representation of a meteorological visibility range $d_{met}$ according to one exemplary embodiment of the present invention. Meteorological visibility range $d_{met}$ results from the distance at which an object is still perceivable with 5% of its original contrast. FIG. 3 thus shows a silhouette of a vehicle 300 in five views next to one another, the contrast varying, from an original contrast referred to as 100% to a contrast referred to as 2%. Between them, the silhouette is shown with 50%, 20% and 5%. The threshold of perception lies at a contrast of 5%.

Figure 4:
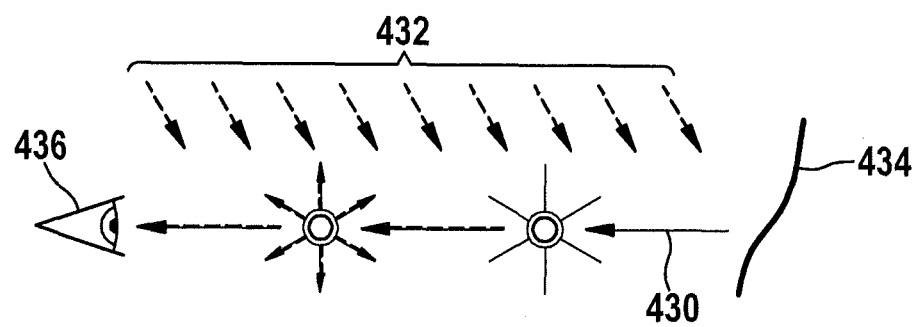
FIG. 4 shows a schematic representation of a correlation between object light and ambient light scattered in according to one exemplary embodiment of the present invention.

FIG. 4 shows a schematic representation of a correlation between object light 430 and ambient light 432 scattered in according to one exemplary embodiment of the present invention. Object light 430 is attenuated on the path from object 434 or item 434 to viewer 436 and enhanced by ambient light 432 scattered in.

The approach described here is based on the tracking of objects, parts of surfaces or points across two or more frames or images of a camera. When these tracked entities—here denoted with reference numeral 434—are moved in their distance relative to the camera, the luminance or object luminance is modified by the fog. Luminance here is to mean not only the classic photometric luminance. Here, the term is to represent any arbitrary (but over the course of the embodiments constant) spectral weighting of radiation density. Luminance may here in particular also represent the spectral weighting according to the sensitivity curve of individual pixels of the camera imager or of the image detection device.

This correlation between luminance and object distance is described in more detail by Koschmieder's theory of horizontal visual range, for example:

$$L = e^{-Kd} L_0 + (1 - e^{+Kd}) L_{air} \qquad (2)$$

parameters $L_0$ and $L_{air}$ representing the luminance of the object and the ambient light, and d [m] representing the distance between object and viewer. L is the object light perceived by the viewer, which is composed according to equation (2) of attenuated object light $L_0$ and ambient light $L_{air}$ scattered in.

According to one exemplary embodiment, when a road sign is tracked during passing by a front camera during fog, the luminance (perceived lightness) decreases when approaching the road sign since less ambient light is scattered into the optical path and the light reflected by the object is weaker than the ambient light. Therefore, a curve of decreasing luminances results during tracking. If the distances to the tracked object are measured simultaneously, the luminance curve may also be plotted over the distance. The distances or spaces to the tracked object may, for example, be measured and determined via "structure from motion" in a mono camera, via stereo vision or via other sensors, for example, LIDAR. One example for a luminance curve over the distance or the space is shown in FIG. 5.

The distances may also be smoothed, interpolated and extrapolated during the process in order to also obtain distances in areas of the track at which a distance estimation is difficult or impossible, but the object may already be tracked. Information about the distance traveled between the recording points in time (for example, using ESP, GPS, ego-motion estimation, . . . ) may be taken into account during the process.

FIG. 4 shows how object light 430 is attenuated on the path from the object to the viewer and enhanced by ambient light 432 scattered in. FIG. 5 shows how the Koschmieder model described here according to equation (2) describes the behavior shown in FIG. 4 by exponentially mixing the light.

Figure 5:
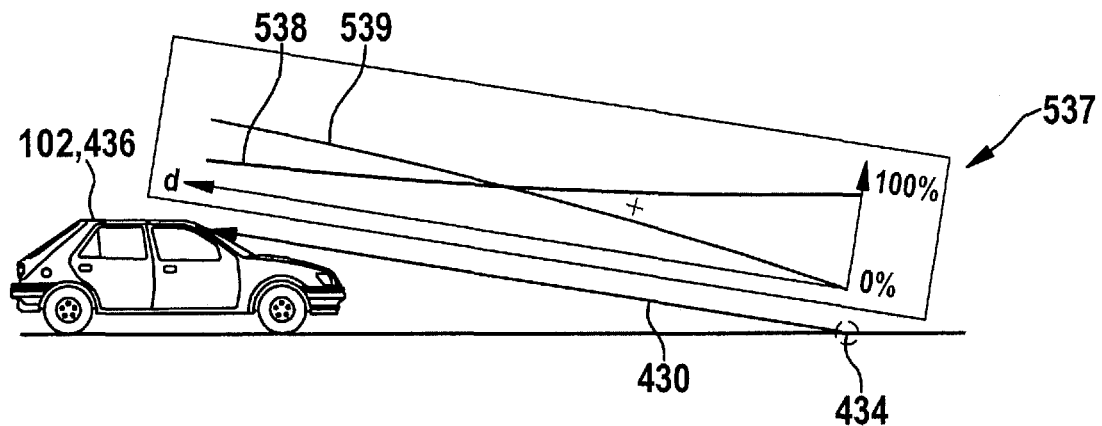
FIG. 5 shows a schematic representation of a correlation between object light and ambient light scattered in according to one exemplary embodiment of the present invention.

FIG. 5 shows a schematic representation of a correlation between object light 430 and ambient light 432 scattered in according to one exemplary embodiment of the present invention. Object light 430 is attenuated on the path from object 434 or item 434 to viewer 436 in a vehicle 102 and enhanced by ambient light 432 scattered in. The diagram in FIG. 5 shows a situation similar to the diagram in FIG. 4. Object 434 is a point or an area of a road surface. A luminance of object light 430 is shown in a Cartesian coordinate system 537, the luminance being plotted in percent over distance d. One first curve 538 shows an exponentially decreasing luminance over distance d of the object light, starting at 100%. Second curve 539 shows an exponentially increasing luminance over distance d of the ambient light, starting at 0%. The ambient light is also referred to as "air light."

In a favorable case, the road surface has a constant albedo within a narrow tolerance range, meaning that the road surface has a constant reflectivity and is diffusely reflecting. In one favorable exemplary embodiment, the road surface follows Lambert's Law, also known as Lambert's cosine law. The radiation density thus remains the same from all viewer angles. For the viewer, this results in a luminance independent of the viewer angle, the luminance being the photometric equivalent to the radiation density.

Figure 6:
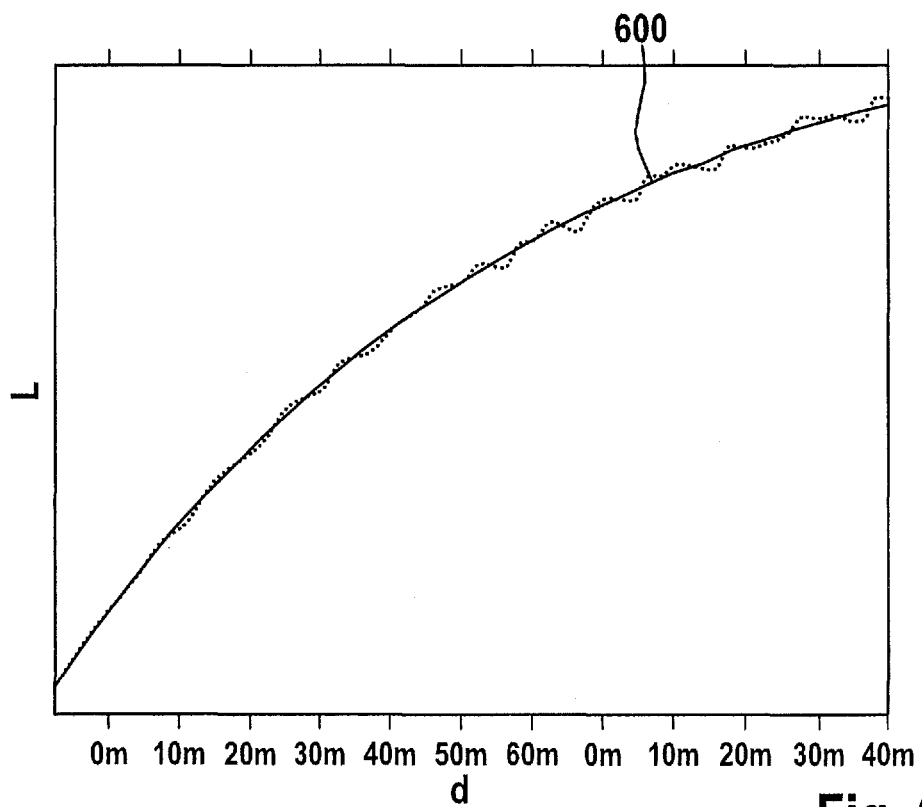
FIG. 6 shows an illustration of measured luminances plotted over a distance according to one exemplary embodiment of the present invention.

FIG. 6 shows an illustration of measured luminances plotted over a distance according to one exemplary embodiment of the present invention. In a Cartesian coordinate system, a distance d is plotted on the abscissa and a luminance L of an object is plotted on the ordinate. Actual measuring points are plotted as dots, i.e., measured luminances of a tracked object, plotted over the distance. An adapted model curve corresponding to Koschmieder's model of horizontal visual range according to equation (2) is shown as a solid line 600.

One way of estimating extinction coefficient K from individual frames or images of a front camera or image detection device during day light is based on the extraction of the so-called "Road Surface Luminance Curve", also abbreviated as RSLC. Here, an area of road and sky is segmented in the camera image and a line-by-line median of the segmented area is plotted as a curve. It has been found that the position of the turning point of this curve may be correlated to extinction coefficient K via models.

Figure 7:
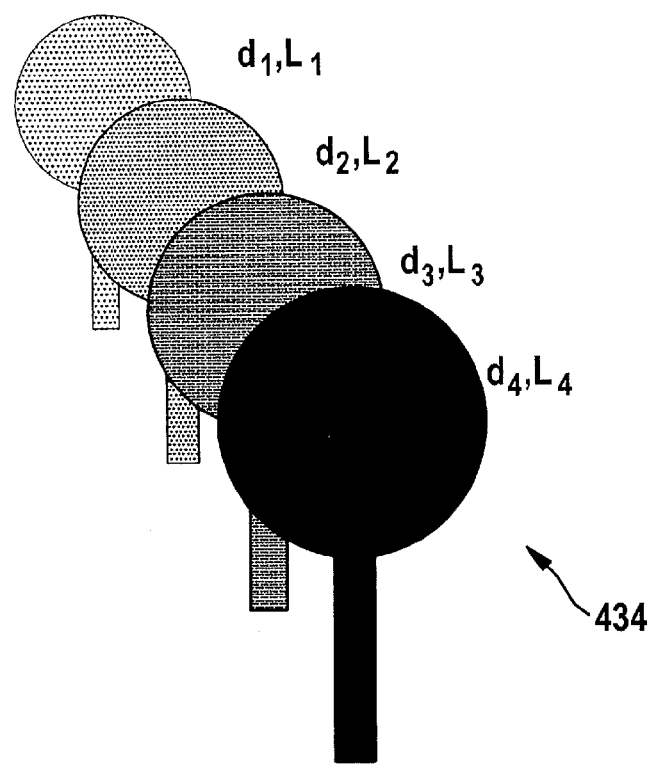
FIG. 7 shows a schematic representation of an object at different distances according to one exemplary embodiment of the present invention.

FIG. 7 shows a schematic representation of an object 434 at different distances according to one exemplary embodiment of the present invention. Luminances of an object are detected at different distances. An object may be understood to mean a diagram in an image of a depiction of a real item. The luminance is referred to as L, the space or the distance as d. The indices refer to the point in time; $L_1$ represents the luminance at a first point in time, $L_2$ represents the luminance at a second point in time. An image is assigned to each point in time.

Thus the value pairs $(L_1; d_1), \ldots, (L_N; d_N)$ result in an object, N being the number of the frames or images in which the object was able to be tracked. In order to make an inference using Koschmieder's model according to equation (2) or also other models regarding the underlying extinction coefficient K, it is recommended that the value pairs correspond to the given model as much as possible; for Koschmieder:

$$L_1 = e^{-Kd_1}L_0 + (1 - e^{-Kd_1})L_{air}, \quad (3)$$
$$\vdots$$
$$L_N = e^{-Kd_N}L_0 + (1 - e^{-Kd_N})L_{air}$$

Since equation system (3) for N>3 based on noisy real data generally cannot be solved accurately, the parameters (K; $L_0$; $L_{air}$) are estimated in such a way that equations (3) within the sense of the least error squares are fulfilled as best possible:

$$\sum_{n=1}^{N} ([e^{-Kd_n}L_0 + (1 - e^{-Kd_n})L_{air}] - L_n)^2 \to \min \quad (4)$$

Extinction coefficient K, in particular, also meteorological visibility range $d_{met}$, may thus be estimated from image sequences.

Figure 8:
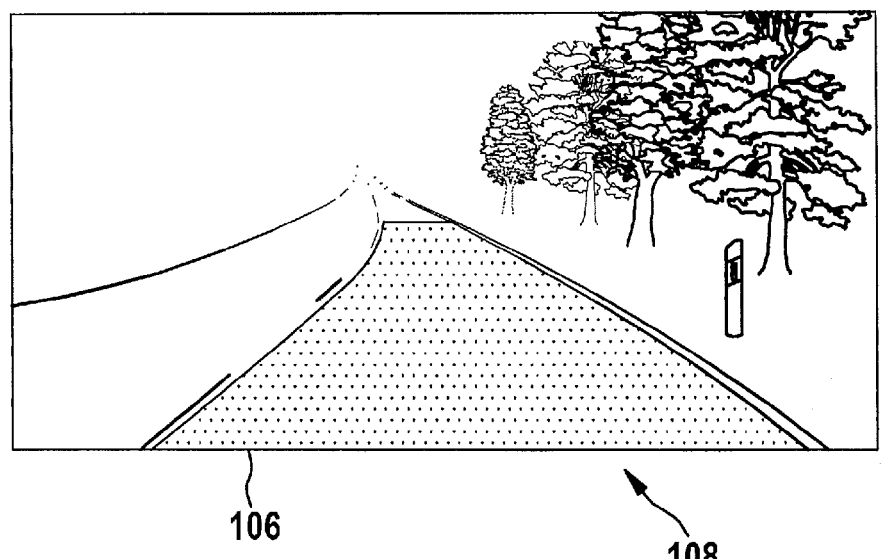
FIG. 8 shows an illustration of surroundings of a vehicle including a segmentation of a road surface according to one exemplary embodiment of the present invention.

FIG. 8 shows an illustration of surroundings of the vehicle having a segmentation of a road surface according to one exemplary embodiment of the present invention. The diagram may be an image 108 of an image detection device of a vehicle. Such an image detection device is shown, for example, in FIG. 1. A depiction 106 of the road was ascertained and is marked. The road essentially extends perpendicular in the image. Parts of the road surface are, due to fog, detectable only to a limited extent and are not taken into further account during the segmenting. This applies to a road section near the horizon. These limitations may also be caused by blocking objects, for example, vehicles or curves.

As described with reference to FIG. 1 or 2, the depiction of the road is segmented and value pairs of object luminance and distance are ascertained in order to determine an atmospheric extinction coefficient K and thus a visibility range $d_{met}$.

Figure 9:
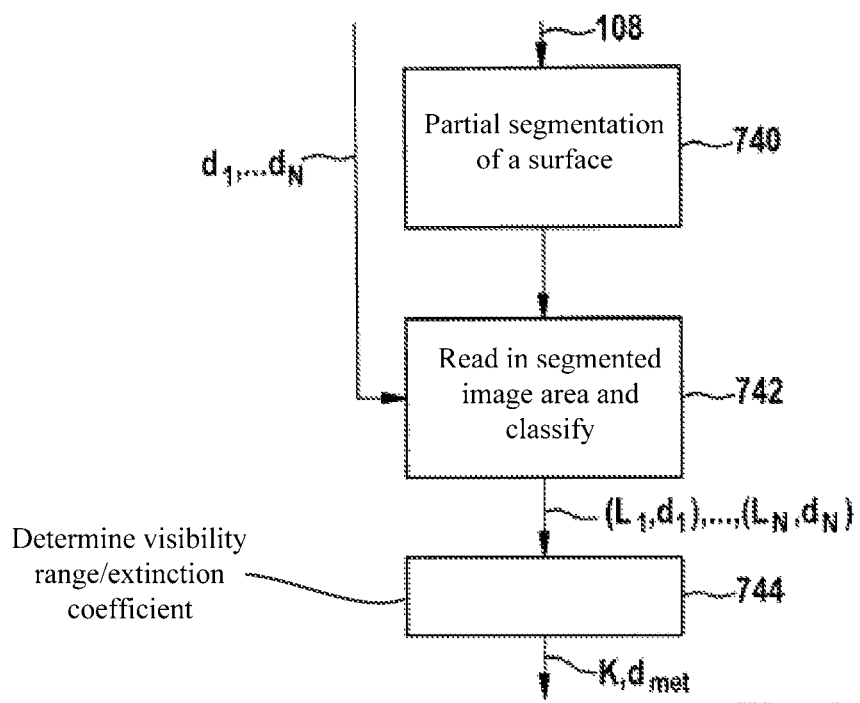
FIG. 9 shows a block diagram of a signal curve according to one exemplary embodiment of the present invention.

FIG. 9 shows a block diagram of a signal curve according to one exemplary embodiment of the present invention. In a first block 740, a partial segmentation of a surface having z-extension/depth extension, for example, a road, is carried out in an image 108 from an image detection device in order to obtain at least one segmented image area. In a following second block 742, the at least one segmented image area as well as distances $d_1, \ldots, d_N$ are read in and a classification/binning into representative luminance-distance-pairs is carried out, for example, line by line. The corresponding results $(L_1, d_1), \ldots, (L_N, d_N)$ are transmitted to a third block 744 in which a rapid Koschmieder model fit is carried out in order to determine a visibility range $d_{met}$ or an extinction coefficient K.

One camera is arranged in such a way that it is oriented along a surface having z-extension/depth extension (for example, a road). This means that multiple visible points exist at the surface which are at different distances to the camera. The surface is preferably Lambertian, has a preferably constant albedo and has preferably an extension over a large area for stability reasons. The scene is furthermore preferably evenly lit (this is the case, for example, during the day.) The camera supplies an image (signal) on which a preferably large area of the surface is segmented. This means that it is decided for each pixel of the image whether this pixel is part of the surface or not. In one exemplary embodiment, this is not carried out exactly. In particular large parts of the surface are classified as "not belonging to the surface" in one exemplary embodiment.

Distances are estimated in the segmented area. Additional information from external sensors and/or other image processing devices and/or assumptions about the surroundings may thereby also be considered. At points of unknown distance it is also interpolated and/or distances are supplemented using assumptions about the surface.

In order to prevent noise in the image or in distances and to render the data manageable for the visibility range estimation, the segmented area is combined into luminance-distance-pairs $(L_1; d_1), \ldots, (L_N; d_N)$. This may take place line by line, for example, with the assumption that the surface is hardly rotated with reference to the camera and that the intersection of an image line with the surface is approximately at a distance to the image detection device.

Parameters K;$L_{air}$;$L_0$ in Koschmieder's model according to equation (2) are adapted in the next step to the luminance-distance-pairs. This is carried out within the sense of the least error squares so that functional $$\mathcal{F}: (K, L_{air}, L_0) \to \sum_{n=1}^{N} ([e^{-Kd_n}L_0 + (1 - e^{-Kd_n})L_{air}] - L_n)^2 \quad (5)$$

is minimized. K or $d_{met}$ is thus estimable from the data. Since this is generally a computationally very intensive step, a special method is used in order to carry out the model adaptation to the surroundings data computationally, preferably cost-effectively:

In order to minimize functional $\mathcal{F}$ (see Equation 6), great effort is required with the aid of conventional methods (Gradient descent, Newton's method, Levenberg-Marquardt algorithm, . . . ) (depending on the number of N, the number of M of the objects and the length of object track $N_m$.) This minimization would be integratable into a real-time system only with great difficulty and would use many resources there. In this exemplary embodiment, a system is described which instead of a minimization of functional $\mathcal{F}$ carries out an equivalent resolution thereto of a one-dimensional equation f(K)=0. Depending on the effort for the calculation of one-dimensional equation f(K), this is a much more cost-effective problem. For solving f(K)=0, the iterative Newton's method K:=K−f(K)/f'(K) may be used, for example. For one-dimensional equation f presented below, few iterations suffice with starting value K:=0 for a sufficient precision of all forms of (simulated) data sets.

A one-dimensional equation f which fulfils the required property may be calculated as follows:

$$f(K) = \qquad (6)$$
$$L_{air}^2(S_{eed} - S_{ed}) + L_{air}(L_0 S_{ed} - 2L_0 S_{eed} + S_{Led}) + L_0 L_0 S_{eed} - L_0 S_{Led},$$

Where $$L_0 = \frac{S_{Le} + L_{air}(S_{ee} - S_e)}{S_{ee}}, \qquad (7)$$

and $$L_{air} = \frac{S_L S_{ee} - S_e S_{Le}}{S_1 S_{ee} - S_e S_e}, \qquad (8)$$

as well as an abbreviated notation is used:

$$S_1 := \sum_{n=1}^{N} 1 \qquad (9)$$

$$S_e := \sum_{n=1}^{N} e^{-K d_n},$$

$$S_{ee} := \sum_{n=1}^{N} e^{-K d_n} e^{-K d_n},$$

$$S_L := \sum_{n=1}^{N} L_n,$$

$$S_{Le} := \sum_{n=1}^{N} L_n e^{-K d_n},$$

$$S_{ed} := \sum_{n=1}^{N} d_n e^{-K d_n},$$

$$S_{eed} := \sum_{n=1}^{N} d_n e^{-K d_n} e^{-K d_n}.$$

Moreover, the inference of extinction coefficient K (required for Newton's method) from one-dimensional equation f is trivially determinable.

In one exemplary embodiment, measuring uncertainties may be taken into account in the functional and thus be taken into account in the parameter estimation. For measuring uncertainties, which are expressed as standard deviations $\sigma_1, \ldots, \sigma_N$ in the measurements $L_1, \ldots, L_N$, the following maximum likelihood objective functional would result for an underlying normally distributed random process, for which an f for the more rapid minimization exists similarly to equations (6), (7), (8) and (9):

$$\mathcal{F}: (K, L_{air}, L_0) \to \sum_{n=1}^{N} \frac{1}{\sigma_n^2} ([e^{-e K d_n} L_0 + (1 - e^{-K d_n}) L_{air}] - L_n)^2 \qquad (10)$$

Since the determination of the luminance from the image intensity is only possible using exact radiometric or photometric calibration of the camera, luminance L may here also represent a (approximately) linear representation of the luminance, i.e., L=α·luminance+β.

Saturation and quantification effects, as well as other inaccuracies in the linear camera model represent no problem. This is since, on the one hand, a linearly transformed representation of the luminance represents no problem for the estimation of extinction coefficient K using the above-mentioned method. And, on the other hand, the relatively small inaccuracies due to quantification and similar effects due to the estimation do not result in any important distortion of the result per error square. A saturation may furthermore be detected and saturated measured luminances may be ignored during the extinction coefficient estimation or K estimation.

In one alternative exemplary embodiment, the method is expanded to multiple surfaces. During the minimization of F, parameters or barriers for parameters are also predefined or inserted into the functional using additional penalty terms (for example, in the form of $(L_{air} - L_{air}^{given})^2$) as prior knowledge. The estimation is thus advantageously stabilized.

Figure 10:
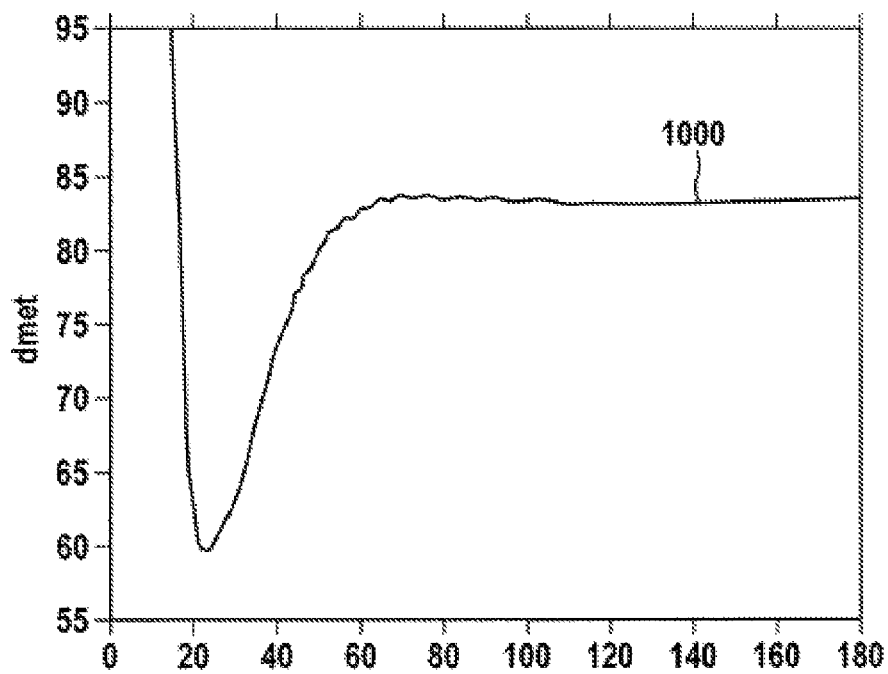
FIG. 10 shows an illustration of estimated visibility ranges as a function of a distance according to one exemplary embodiment of the present invention.

FIG. 10 shows an illustration of estimated visibility ranges as a function of a distance according to one exemplary embodiment of the present invention. FIG. 10 thus shows an estimated visibility range of 1000 in a Cartesian coordinate system as a function of the maximum distance to which the road could be segmented. In this real example, the visibility range estimation becomes unstable below 50 m (however, initially still within acceptable error bounds.) A maximum distance of a segmentation of the road is shown on the abscissa; a meteorological visibility range $d_{met}$ is shown on the ordinate. A local minimum of the curve is situated at a distance of 20 meters, the curve subsequently rising until a distance of 50 to 60 meters to then represent a nearly constant visibility range. As a function of the quality of the measured data, very different curve progressions are possible here.

Figure 11:
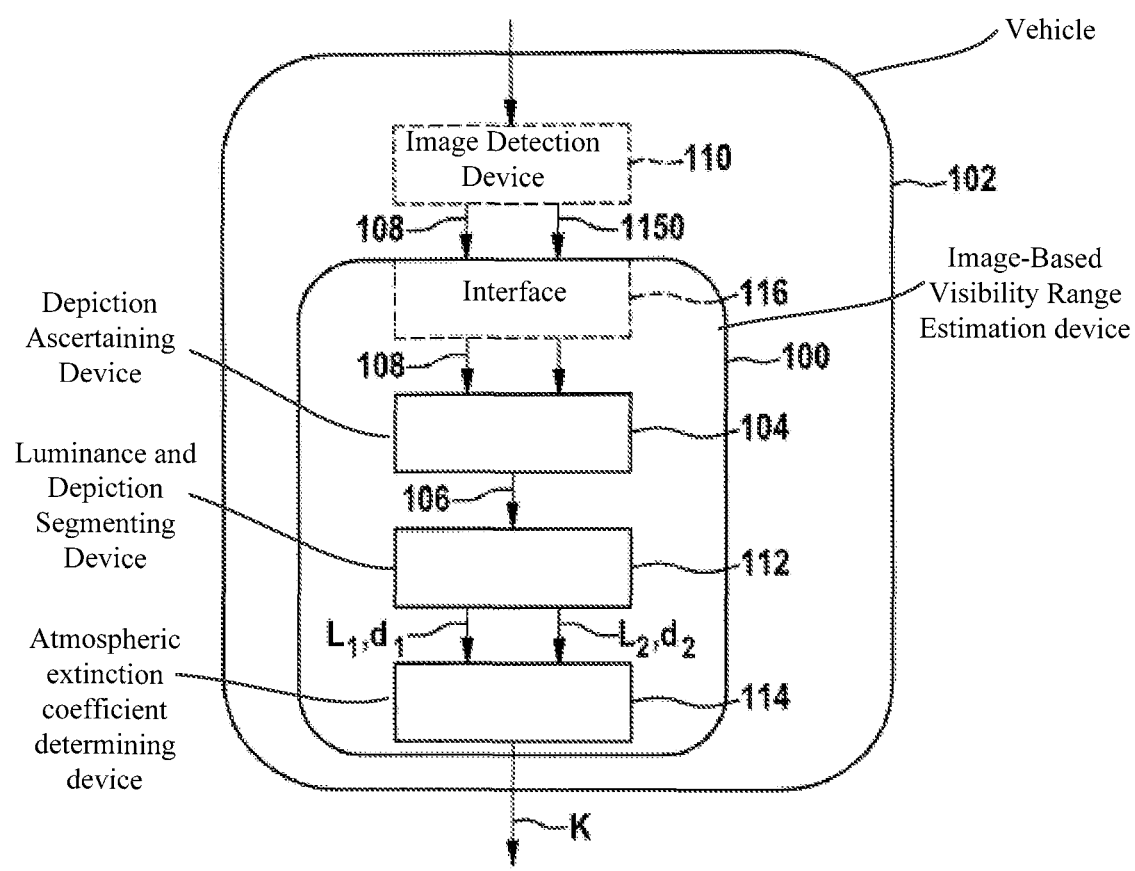
FIG. 11 shows a block diagram of a device for the image-based visibility range estimation for a vehicle according to one exemplary embodiment of the present invention.

FIG. 11 shows a block diagram of a device 100 for the image-based visibility range estimation for a vehicle 102 according to one exemplary embodiment of the present invention. Device 100 may be an exemplary embodiment of device 100 shown in FIG. 1. Device 100 is expanded by one processing of at least one second image 1150 of image detection device 110. Second image 1150 shows a depiction of the surroundings of vehicle 102 at a second point in time. The second point in time differs from a first point in time at which first image 108 was detected. In the exemplary embodiment shown, the second point in time sequentially follows the first point in time. FIG. 11 shows a device 100 for the combined, image-based and tracking-based visibility range estimation. A method for the image-based visibility range estimation, as described in FIG. 2, is thus combined with a method for the tracking-based visibility range estimation.

The diagram of device 100 essentially corresponds to the diagram and description of device 100 for the image-based visibility range detection in FIG. 1, with the difference that the image detection device detects at least two images sequentially, and provides them to device 100 via interface 116 for reading in images.

Device 104 for ascertaining is designed to track an object in first image 108 detected at the first point in time and in second image 1050 detected at the second point in time. Device 112 for segmenting is designed to ascertain at least one third object luminance $L_3$ of the object and a third distance $d_3$ to the object at the second point in time in addition to the value pairs of first object luminance $L_1$, first distance $d_1$, second object luminance $L_2$ and second distance $d_2$ at the first point in time. Determination device 114 is designed to ascertain atmospheric extinction coefficient K using first object luminance $L_1$, second object luminance $L_2$, at least third object luminance $L_3$, first distance $d_1$, second distance $d_2$ and third distance $d_2$, atmospheric extinction coefficient K being directly correlated to visibility range $d_{met}$.

In one optional exemplary embodiment, a plurality of value pairs of object luminance L and distance d are ascertained per image and provided to determination device 114. Furthermore, in one optional exemplary embodiment, a plurality of images are sequentially detected at a plurality of points in time and analyzed. For example, a sequence of 10, 30 or 50 images is analyzed.

FIG. 11 shows a device which estimates K (during daylight) particularly rapidly or real-time-capably from a partially segmented surface (for example, a road) and distance data. In one exemplary embodiment, this is combined with a method for the visibility range estimation, which estimates extinction coefficient K from individual frames or images of a front camera or an image detection device during daylight. One method with which the method for visibility range estimation presented here may be combined is based on the extraction of the so-called "Road Surface Luminance Curve" (RSLC). Here, an area of road and sky is segmented in the camera image and a line-by-line median of the segmented area is plotted as a curve. It has been found that the position of the turning point of this curve may be correlated to K using models.

In one exemplary embodiment, the method presented here, or the device, is combined with an additional approach to estimate the visibility range based on a model. This is based on the tracking of objects across multiple frames. The measured luminances L and distances d of the objects are approximated using a model which includes extinction coefficient K as a parameter. In this way, extinction coefficient K is estimated as the most likely parameter among the monitored measurements. One model for this is typically the model of horizontal visual range by Koschmieder according to equation (2), which is combined with a method for rapid estimation.

Parameters $L_0$ and $L_{air}$ represent the luminance of the object and the ambient light and d [m] represents the distance between object and viewer. L is the object light perceived by the viewer, which is composed accordingly of attenuated object light and ambient light scattered in.

In one variant, the method described here is expanded to multiple surfaces. During the minimization of F, parameters or barriers for parameters are also predefined or inserted into the functional using additional penalty terms as prior knowledge.

The exemplary embodiments described here and illustrated in the figures are selected only as examples. Different exemplary embodiments may be combined with each other completely or in regard to individual features. One exemplary embodiment may also be supplemented by features of another exemplary embodiment.

Furthermore, the method steps presented here may also be repeated or carried out in a sequence different from the sequence described.

If one exemplary embodiment includes an "and/or" link between a first feature and a second feature, this should be read in such a way that the exemplary embodiment according to one specific embodiment includes both the first feature and the second feature, and according to an additional specific embodiment includes either only the first feature or only the second feature.

What is claimed is:

1. A method for an image-based visibility range estimation, comprising:
    obtaining, by processing circuitry, an image captured by an image detection device and that depicts surroundings of the image detection device; processing, by the processing circuitry, the image, wherein the processing includes: ascertaining, by processing circuitry, a depiction of an object in the image; and segmenting, by the processing circuitry, the depiction of the object in order to (i) obtain a first object range of the object having an equal first distance to the image detection device within a tolerance range, (ii) obtain a second object range of the object having an equal second distance to the image detection device within a tolerance range, (iii) determine a first object luminance for the first object range, and (iv) determine a second object luminance for the second object range; and determining, by the processing circuitry, an atmospheric extinction coefficient using (a) the first object luminance, the second object luminance, the first distance, and the second distance with (b) at least one of (i) a one-dimensional equation and (ii) a model for light transmission by atmospheric aerosols, wherein the atmospheric extinction coefficient is in direct correlation to the visibility range.

2. The method as recited in claim 1, wherein in the step of determining, the extinction coefficient is determined using an estimation method from the one-dimensional equation.

3. The method as recited in claim 1, wherein in the step of determining, the extinction coefficient is determined using an iterative Newton's method.

4. The method as recited in claim 1, wherein:
    in the step of segmenting, the depiction of the object is segmented in order to (i) further obtain at least one third object range having an equal third distance to the image detection device within a tolerance range, and (ii) further determine a third object luminance for the third object range is determined; and
    the atmospheric extinction coefficient is determined additionally using the third object luminance and the third distance.

5. The method as recited in claim 1, further comprising:
    a step of detecting the image using the image detection device, the image showing a depiction of an object of the surroundings in the image, the object having an extension at least along a direction of travel of the vehicle.

6. The method as recited in claim 1, wherein the steps of ascertaining and segmenting are carried out for an additional image, the atmospheric extinction coefficient being determined in the step of determining using at least one third object luminance and a third distance assigned to third object luminance.

7. A device for an image-based visibility range estimation, comprising:
    a control unit including a processor configured to perform the following:
        ascertaining a depiction of an object in an image, the image showing a depiction of surroundings of an image detection device;
        segmenting the depiction of the object in order to (i) obtain a first object range of the object having an equal first distance to the image detection device within a tolerance range, (ii) obtain a second object range of the object having an equal second distance to the image detection device within a tolerance range, (iii) determine a first object luminance for the first object range, and (iv) determine a second object luminance for the second object range; and determining an atmospheric extinction coefficient using (a) the first object luminance, the second object luminance, the first distance, and the second distance with (b) at least one of (i) a one-dimensional equation and (ii) a model for light transmission by atmospheric aerosols, wherein the atmospheric extinction coefficient is in direct correlation to the visibility range.

8. A non-transitory, computer-readable data storage medium storing a computer program having program codes which, when executed on a computer, perform a method for an image-based visibility range estimation, the method comprising:

ascertaining a depiction of an object in an image, the image showing a depiction of surroundings of an image detection device;

segmenting the depiction of the object in order to (i) obtain a first object range of the object having an equal first distance to the image detection device within a tolerance range, (ii) obtain a second object range of the object having an equal second distance to the image detection device within a tolerance range, (iii) determine a first object luminance for the first object range, and (iv) determine a second object luminance for the second object range; and determining an atmospheric extinction coefficient using (a) the first object luminance, the second object luminance, the first distance, and the second distance with (b) at least one of (i) a one-dimensional equation and (ii) a model for light transmission by atmospheric aerosols, wherein the atmospheric extinction coefficient is in direct correlation to the visibility range.

* * * * *